(12) United States Patent
Ci

(10) Patent No.: US 10,434,066 B2
(45) Date of Patent: Oct. 8, 2019

(54) SOLID DRINK FOR REGULATING YANG-DEFICIENCY CONSTITUTION AND PROCESSING METHOD THEREOF

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/878,374

(22) Filed: Jan. 23, 2018

(65) Prior Publication Data

US 2019/0160010 A1     May 30, 2019

(30) Foreign Application Priority Data

Nov. 30, 2017 (CN) .......................... 2017 1 1242621

(51) Int. Cl.
| | | |
|---|---|---|
| *A61K 36/00* | (2006.01) |
| *A61K 9/16* | (2006.01) |
| *A61K 36/535* | (2006.01) |
| *A61K 36/815* | (2006.01) |
| *A61K 36/73* | (2006.01) |
| *A61K 36/54* | (2006.01) |
| *A61K 36/235* | (2006.01) |
| *A61K 36/9068* | (2006.01) |
| *A61K 9/00* | (2006.01) |
| *A23L 2/02* | (2006.01) |
| *A23L 2/60* | (2006.01) |
| *A23L 29/212* | (2016.01) |
| *A61K 36/076* | (2006.01) |
| *A23L 2/08* | (2006.01) |
| *A23L 2/39* | (2006.01) |

(52) U.S. Cl.
CPC ............... *A61K 9/1682* (2013.01); *A23L 2/02* (2013.01); *A23L 2/08* (2013.01); *A23L 2/39* (2013.01); *A23L 2/60* (2013.01); *A23L 29/212* (2016.08); *A61K 9/0095* (2013.01); *A61K 9/1617* (2013.01); *A61K 9/1652* (2013.01); *A61K 36/076* (2013.01); *A61K 36/235* (2013.01); *A61K 36/535* (2013.01); *A61K 36/54* (2013.01); *A61K 36/73* (2013.01); *A61K 36/815* (2013.01); *A61K 36/9068* (2013.01); *A23V 2002/00* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue

(57) ABSTRACT

Provided is a solid drink for regulating yang-deficiency constitution. The solid drink includes the following components of raw materials in parts by weight: *Perilla* 30-60, raspberry 35-55, *Lycium barbarum* 35-57, poria 30-54, cinnamon 35-55, fennel 20-40, ginger 33-55, dextrin 50-90, maltodextrin 23-45, soluble starch 20-44, and aspartame 0.15-0.35. The solid drink is easy to manufacture, and all the raw materials used are medicine materials of medicinal and edible dual purposes, and all the excipients used also satisfy national standard GB2760-2011 (National Food Safety Standard for Uses of Food Additives). It is safe to eat (drink) with good taste, and long-term consumption has certain effects on improving the yang-deficiency constitution. Moreover, the processing process is suitable for industrial mass production.

11 Claims, 2 Drawing Sheets

SOLID DRINK FOR REGULATING YANG-DEFICIENCY CONSTITUTION AND PROCESSING METHOD THEREOF

CROSS-REFERENCE TO RELATED APPLICATIONS

This application claims priority under 35 U.S.C. § 119 to a Chinese Patent Application No. 201711242621.0 filed Nov. 30, 2017, in the State Intellectual Property Office of China, the entire contents of which are hereby incorporated by reference.

TECHNICAL FIELD

The present invention relates to the field of health food, and particularly to a solid drink for regulating yang-deficiency constitution and a processing method thereof.

BACKGROUND

According to "Classification and Determination of Constitution in TCM" by China Association of Chinese Medicine, the constitution of human bodies includes nine types, namely, balanced constitution (constitution of yin-yang harmony), yang-deficiency constitution, yin-deficiency constitution, qi (vital energy)-deficiency constitution, phlegm-dampness (tanshi) constitution, dampness-heat constitution, qi-stagnation constitution, blood-stasis constitution, and allergic (special, tebing) constitution. Most of them belong to sub-health status.

The yang-deficiency constitution manifests insufficiency of yang-qi in the body and interior cold due to yang deficiency when the internal organs (zang and fu) of the human body dysfunction, usually showing pale facial complexion, weak breath, physical tiredness and somnolence, aversion to cold and chilly limbs, general weakness or limb edema, pale and fat tongue with indentation, slightly white tongue fur, deep pulse and inertia, and is mostly caused by insufficient inborn endowment, in addition to outside pathogenic cold and eating too much cold food, extreme anxieties, and sexual strain, after long illness. When being attacked, the yang-deficiency patients tend to develop diseases such as phlegm, swelling, and diarrhea, prefer summer to winter, and are vulnerable to wind, cold, and dampness pathogen.

The yang-deficiency constitution, being a sub-health constitution, belongs to chronic conditions with a relatively long course, and requires long-term administration and gradual regulation so as to achieve the effects of nourishing and enriching qi. The common Chinese medicine dosage form includes decoction and Chinese patent drug such as pills. The decoction has a better efficacy, but is tedious to take, and the taste thereof is also bad. It is not easy for patients to persistently take decoction for a long period of time, while the efficacy of pills is relatively poor.

Food is the best for preventing diseases and keeping healthy for human beings. "Homology between medicine and food" is one of the most valuable contributions of original Chinese medical science to the human beings. According to "Rites of Zhou•Tianguan•Curing sickness", curing diseases by combining five tastes, five cereals, and five medicines, which indicates the physiological health-care function of food. A method of regulating organism using properties of food to get healthy or cure diseases is called as food therapy (nutrition therapy, dietary therapy). However, "nourishment" is better than "therapy". Dietary nourishment refers to nourishing by combining nutritional effects of food with the physical condition of the body to enhance resistibility and immunity, and further to prolong life and have a strong physique. According to "Qian Jin Prescriptions", a doctor should firstly know the source of a disease and symptoms, then treat the disease with corresponding food. If the disease cannot be cured through food therapy, then a medicine is used. It can be seen that the application of food therapy is not only the basic treatment means of doctors at that time, but also an important ground for evaluating whether a doctor has excellent medical skills.

It is proposed in "Huangdi Neijing" that "making preventive treatment before getting illness is the top-class medical skill, performing treatment when illness is suspected is the middle-class medical skill, and performing treatment when illness is present is the lower-class medical skill". "Making preventive treatment before getting illness" refers to taking corresponding measures to prevent occurrence and development of illness. The constitution determines our health and susceptibility to diseases. In the face of various diseases, increasingly low morbidity age, and more and more sub-healthy population, the food therapy is favored by more and more consumers due to its advantages of being healthy and natural. With regard to problems easily arising, it is of critical significance to develop a type of food having the function of maintaining good health and regulating yang-deficiency constitution with good taste by combining the precious experience of traditional Chinese health care and accumulation of good aspects of keeping the balanced constitution of the traditional Chinese medicine, using technologies and methods of modern sciences, based on the homology between medicine and food.

DISCLOSURE OF THE INVENTION

A main object of the present invention is to provide a health-care food for regulating yang-deficiency constitution.

In order to achieve the above object, according to one aspect of the present invention, a solid drink for regulating yang-deficiency constitution is provided.

The solid drink for regulating yang-deficiency constitution according to the present invention includes the following components of raw materials in parts by weight: *Perilla* 30-60, raspberry 35-55, *barbarum* 35-57, poria 30-54, cinnamon 35-55, fennel 20-40, ginger 33-55, dextrin 50-90, maltodextrin 23-45, soluble starch 20-44, and aspartame 0.15-0.35.

Furthermore, the solid drink for regulating yang-deficiency constitution of the present invention includes the following components of raw materials in parts by weight: *Perilla* 40-50, raspberry 41-49, *Lycium barbarum* 39-51, poria 38-47, cinnamon 41-52, fennel 25-35, ginger 37-50, dextrin 60-80, maltodextrin 27-40, soluble starch 25-39, and aspartame 0.2-0.3.

Furthermore, the solid drink for regulating yang-deficiency constitution of the present invention includes the following components of raw materials in parts by weight: *Perilla* 45, raspberry 45, *Lycium barbarum* 45, poria 45, cinnamon 45, fennel 30, ginger 45, dextrin 69, maltodextrin 34, soluble starch 34, and aspartame 0.25.

In order to achieve the above object, according to another aspect of the present invention, a method for processing a solid drink for regulating yang-deficiency constitution is provided.

The method for processing a solid drink for regulating yang-deficiency constitution according to the present invention includes the following steps:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid;

(3) concentrating: feeding the Chinese medicine liquid obtained in step (2) into a concentrator via a pipeline, to be concentrated into a thick paste;

(4) wet granulating: mixing and stirring dextrin, maltodextrin, soluble starch, and aspartame to obtain a mixed excipient, and adding the thick paste obtained in step (3) to the mixed excipient, then stirring and granulating them.

Furthermore, operations of the twice decocting processes in the above step (2) are as follows:

for the first time, adding water of 10 times the weight of the mixture obtained in the above step (1), heating them for decocting and extracting the same, wherein timing is started when they are boiling, and after 1.5 hours of decoction and extraction, immediately feeding a medicine liquid through a pipeline filter by a pump into a stainless steel medicine liquid tank; for the second time, adding water of 8 times the weight of the mixture obtained in the above step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

Furthermore, the concentration temperature in the above step (3) is 70-80° C., and the relative density of the resulted thick paste is 1.2-1.5 under a temperature condition of 50° C.

Furthermore, the wet granulating in the above step (4) includes the following steps:

(4.1) dry blending: putting dextrin, maltodextrin, soluble starch, and aspartame into an efficient mixing granulator to be mixed and stirred for 15 minutes, to obtain the mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time;

(4.3) drying: putting the sized particles obtained in step (4.2) into a boiling dryer to be dried;

(4.4) sizing for the second time: performing the second time of sizing by an oscillating machine.

Furthermore, a 12-mesh screen is used in the first time of sizing, and a 10-mesh screen is used in the second time of sizing.

Furthermore, in the drying process of step (4.3), a temperature of the materials is kept at 70-80° C., and a moisture of the final materials is kept below 5%.

Furthermore, a step of selecting particles is further included after the second time of sizing, to select particles with 10-60 meshes.

The solid drink of the present invention is easy to manufacture, and all the raw materials used are medicine materials of medicinal and edible dual purposes, and all the excipients used also satisfy national standard GB2760-2011 (National Food Safety Standard for Uses of Food Additives). It is safe to eat (drink) with good taste, and long-term consumption has certain effects on improving the yang-deficiency constitution. Moreover, the processing process is suitable for industrial mass production.

BRIEF DESCRIPTION OF DRAWINGS

The figures constituting a portion of the present application are used for further understanding of the present invention, so as to make it more obvious other features, objects, and advantages of the present application. Exemplary examples of the present application, drawings, and description thereof are used to explain the present invention, rather than improperly limiting the present invention. In the figures.

DETAILED DESCRIPTION OF EMBODIMENTS

Figure 1:
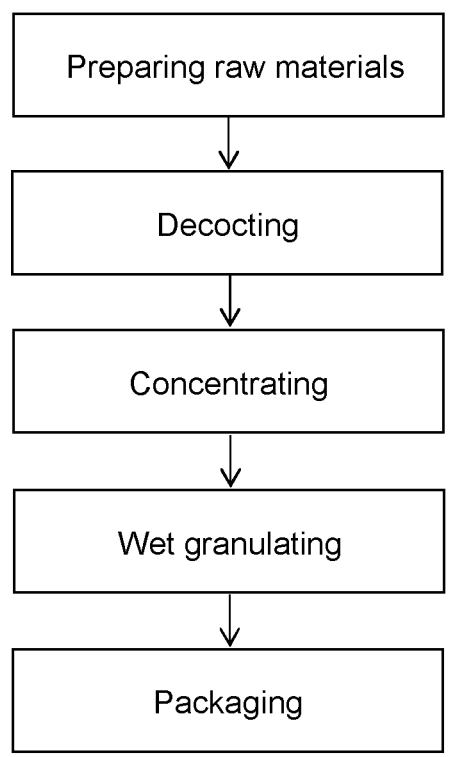
FIG. 1 shows a processing process of a solid drink according to an example of the present invention.

In order to make a person skilled in the art better understand solutions of the present application, below technical solutions of the examples of the present application will be described clearly and completely in conjunction with figures of the examples of the present application. Apparently, some but not all of examples of the present application are described. Based on the examples of the present application, all the other examples, which a person ordinarily skilled in the art obtains without paying inventive effort, fall within the scope of protection of the present application.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present application and features in the examples can be combined with each other without conflict. The present application will be described in detail with reference to the figures in conjunction with the examples.

A main object of the present invention is to provide a health-care food for regulating yang-deficiency constitution.

In order to realize the above object, according to one aspect of the present invention, a solid drink for regulating yang-deficiency constitution is provided.

The solid drink for regulating yang-deficiency constitution according to the present invention includes the following components of raw materials in parts by weight: *Perilla* 30-60, raspberry 35-55, *Lycium barbarum* 35-57, poria 30-54, cinnamon 35-55, fennel 20-40, ginger 33-55, dextrin 50-90, maltodextrin 23-45, soluble starch 20-44, and aspartame 0.15-0.35.

*Perilla*: perilla, astringent in taste and warm in nature, exerts the curative effect through the lung and spleen channels, relieves exterior syndrome by diaphoresis, regulates qi and the middle energizer, and detoxifies ciguatoxin and crab poison, and is used for treatment of common cold due to wind-cold, headache, cough, thoracico-abdominal distention, and fish and crab poisoning.

Raspberry: raspberry, sweet and sour in taste, and warm in nature, exerts the curative effect through the liver, kidney, and urinary bladder channels, tonifies kidney to strengthen essence and reduce urination, and nourishes the liver to improve eyesight, and is used for treatment of gonobolia and spermatorrhea, enuresis and frequent urination, impotence and premature ejaculation, and blurring and dim vision.

*Lycium barbarum*: *Lycium barbarum*, sweet in taste and mild in nature, exerts the curative effect through the liver and kidney channels, nourishes the livers and kidneys, and replenishes vital essence to improve eyesight, and is used for treatment of syndromes of liver-kidney yin deficiency. *Lycium barbarum* is sweet and natural in taste and moist, nourishes the livers and kidneys, with the function of nourishing and building up the body, and can be applied to various syndromes of liver-kidney yin deficiency.

Poria: poria, sweet and light in taste, and mild in nature, exerts the curative effect through the heart, lung, spleen, and kidney channels, eliminates dampness and promotes diuresis, tonifies the spleens, and calms the heart, and is used for treatment of edema and oliguria, phlegm-fluid retention, reduced spleen-deficiency appetite, loose stool diarrhea, unease, and palpitation and insomnia.

Cinnamon: cinnamon, astringent and sweet in taste and extremely hot in nature, exerts the curative effect through the kidney, spleen, heart, and liver channels, has the efficacy of tonifying fire and helping yang, guiding fire to origin, eliminating cold to stop pain, and warming the meridians, and is used for treatment of impotence and uterine cold, waist and knee crymodynia, kidney deficiency asthma, yang deficiency with upper manifestation, dizziness and hot eyes, heart and abdomen crymodynia, deficiency-cold vomiting and diarrhea, cold abdominal colic stomachache, dysmenorrhea and amenorrhea.

Fennel: fennel, astringent in taste and warm in nature, exerts the curative effect through the liver, kidney, bladder, and stomach channels, warms the kidney and liver, promotes the circulation of qi to relieve pains, and harmonizes stomach, and is mainly used for treatment of cold abdominal colic stomachache, testicle sagging, abdominal fullness crymodynia, reduced appetite and vomit, hypochondriac pain, kidney-deficiency lumbago, and dysmenorrhea.

Ginger: ginger, astringent in taste and hot in nature, exerts the curative effect through the spleen, stomach, kidney, heart, and lung channels, warms the middle energizer for dispelling cold, restores yang and promotes coronary circulation, warms the lungs, and resolves fluid, and is used for the treatment of abdominal fullness crymodynia, vomit, diarrhea, cold limbs, faint pulse, cold fluid, cough and asthma.

The yang-deficiency constitution is mostly caused by dysfunctions of internal organs such as insufficient inborn endowment, outside pathogenic cold, eating too much cold food, extreme anxieties, prolonged illness, and sexual strain, "with yang waning and yin waxing", generating interior cold due to excess cold yin-qi, showing insufficiency of yang-qi, reduced functions of the body such as warming, promoting, evaporation, and gasification, even the syndrome of water retention. Regulating the yang-deficiency constitution is based on the principle of warming yang and building up the body. In the present invention, fennel and ginger are used to warmly invigorate the middle energizer; cinnamon is used to warmly invigorate kidney-yang; *Perilla* can dispel cold, promote the circulation of qi, and regulate the middle energizer; poria makes the spleen and stomach transport healthily; raspberry and *Lycium barbarum* can achieve the object of "reinforcing yang from yin" ("reinforcing yang from yin" refers to, for yang-deficiency patients, using medicines for nourishing yin as appropriate while mainly using medicines for tonifying yang, so as to finally achieve the object of tonifying yang by nourishing yin). The yang-qi deficiency of the yang-deficiency constitution can be tonified by combining various medicines. In addition, dextrin, maltodextrin, and aspartame, on one hand, can exert the medicinal value and balance the nutritional ingredients, and on the other hand, also can be used for seasoning.

As shown in FIG. 1, a method for processing a solid drink for regulating yang-deficiency constitution includes the following steps:

(1) preparing raw materials: mixing cinnamon, *Lycium barbarum*, ginger, *Perilla*, raspberry, poria, and fennel having undergone purification, cleansing, cutting, and grinding, for subsequent use, with proportions of respective raw materials being the proportions provided in the present invention;

(2) decocting: decocting twice a mixture obtained in step (1) with addition of water, to obtain a Chinese medicine liquid;

(3) concentrating: feeding the Chinese medicine liquid obtained in step (2) into a concentrator via a pipeline, to be concentrated into a thick paste;

(4) wet granulating: mixing and stirring dextrin, maltodextrin, soluble starch, and aspartame to obtain a mixed excipient, and adding the thick paste obtained in step (3) to the mixed excipient, then stirring and granulating them;

(5) packaging: subjecting a product obtained after the wet granulating to a packaging step, to result in a finished product.

The object of step (1) is to remove fat from the seed Chinese medicine materials ground with a 2-mesh screen; cutting or grinding rhizomatic Chinese medicine materials, enriched in cellulose and starch, to be extracted can effectively reserve target ingredients and prevent expansion of polysaccharides; purification can remove impurities and soil, and effectively reduce remnant of pollutants such as heavy metals and pesticides.

Operations of the twice decocting processes in the above step (2) are as follows: for the first time, adding water of 10 times the weight of the mixture obtained in the step (1), heating them for decocting and extracting the same, wherein timing is started when they are boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

The concentration temperature in the above step (3) is 70-80° C., and the relative density of the resulted thick paste is 1.2-1.5 under the temperature condition of 50° C. Low-temperature evaporation can effectively reduce decomposition of heat-sensitive components, for example, organic acids such as citric acid, malic acid, and oxalic acid, moreover, it has high concentration efficiency with no discharge of solvent vapor, and facilitates evaporation and airtightness without polluting environment.

Figure 2:
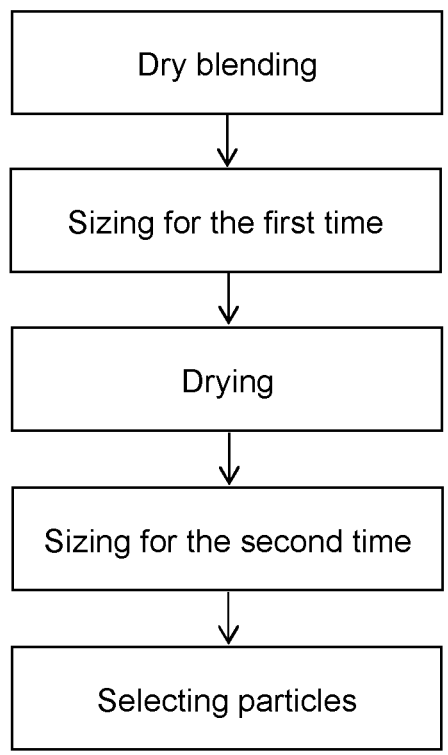
FIG. 2 shows specific steps of wet granulating in a processing process of a solid drink according to an example of the present invention.

As shown in FIG. 2, the wet granulating in the above step (4) includes the following steps:

(4.1) dry blending: putting dextrin, maltodextrin, soluble starch, and aspartame into an efficient mixing granulator to be mixed and stirred for 15 minutes, to obtain the mixed excipient, with proportions of respective raw materials being the proportions provided in the present invention;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time, wherein mixing granulation can preferably prevent separation of various components, and since the segregation phenomenon easily occurs due to differences existing among particle sizes and densities of the components of the mixed extract, the granulation not only can overcome this problem, but also can significantly improve the solubility;

(4.3) drying: putting the sized particles obtained in step (4.2) into a boiling dryer to be dried, wherein the boiling dryer can effectively control the particle size distribution, and control the moisture of the product;

(4.4) sizing for the second time: performing the second time of sizing by an oscillating machine, wherein through the second time of sizing, the particles distribution, bulk density, and compactness can be controlled.

In the above steps, a 12-mesh screen is used in the first time of sizing, and a 10-mesh screen is used in the second time of sizing.

In the drying process of the above step (4.3), the temperature of the materials is kept at 70-80° C., and the moisture of the final materials is kept below 5%. In the present step, a pot can be turned frequently according to the drying situation of the materials, ensuring that the moisture of the final materials meets requirements.

On the basis of the above embodiment, a step of selecting particles is further included after the second time of sizing, to select particles with 10-60 meshes. The appearance and homogeneity of the product particles can be improved by selecting the particles. In practical operation, after the particle selection, a product name, a product lot number, specification, net weight, date of manufacture, name of position, and person in charge are recorded and tagged, and a delivery receipt is filled in, then the product is transferred to an intermediate station.

Example 1

A solid drink for regulating yang-deficiency constitution included the following components of raw materials in parts by weight: *Perilla* 30, raspberry 35, *Lycium barbarum* 35, poria 30, cinnamon 35, fennel 20, ginger 33, dextrin 50, maltodextrin 23, soluble starch 20, and aspartame 0.15.

A preparing method was as follows:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 70° C., and the relative density of the resulted thick paste being 1.2 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 70° C., and the moisture of the final materials being kept at 5%;

(4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag±5%.

Example 2

A solid drink for regulating yang-deficiency constitution included the following components of raw materials in parts by weight: *Perilla* 60, raspberry 55, *Lycium barbarum* 57, poria 54, cinnamon 55, fennel 40, ginger 55, dextrin 90, maltodextrin 45, soluble starch 44, and aspartame 0.35.

A preparing method was as follows:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 80° C., and the relative density of the resulted thick paste being 1.5 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 80° C., and the moisture of the final materials being kept at 3%;

(4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag±5%.

Example 3

A solid drink for regulating yang-deficiency constitution included the following components of raw materials in parts by weight: *Perilla* 50, raspberry 49, *Lycium barbarum* 51, poria 47, cinnamon 52, fennel 35, ginger 50, dextrin 80, maltodextrin 40, soluble starch 39, and aspartame 0.3.

A preparing method was as follows:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 75° C., and the relative density of the resulted thick paste being 1.45 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 78° C., and the moisture of the final materials being kept at 3.4%;

(4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag±5%.

Example 4

A solid drink for regulating yang-deficiency constitution included the following components of raw materials in parts by weight: *Perilla* 40, raspberry 41, *Lycium barbarum* 39, poria 38, cinnamon 41, fennel 25, ginger 37, dextrin 60, maltodextrin 27, soluble starch 25, and aspartame 0.2.

A preparing method was as follows:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 73° C., and the relative density of the resulted thick paste being 1.33 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 72° C., and the moisture of the final materials being kept at 4.5%;

(4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag±5%.

Example 5

A solid drink for regulating yang-deficiency constitution included the following components of raw materials in parts by weight: *Perilla* 45, raspberry 45, *Lycium barbarum* 45, poria 45, cinnamon 45, fennel 30, ginger 45, dextrin 69, maltodextrin 34, soluble starch 34, and aspartame 0.25.

A preparing method was as follows:

(1) preparing raw materials: mixing cinnamon, *Lycium barbarum*, ginger, *Perilla*, raspberry, poria, and fennel having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 77° C., and the relative density of the resulted thick paste being 1.4 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 76° C., and the moisture of the final materials being kept at 3.8%;

(4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag±5%.

Experiment Example 1 below is a test of effects of the solid drink for regulating yang-deficiency constitution prepared in Example 5 of the present invention.

Basic situation of cases: there were 90 cases of yang-deficiency constitution, 45 males, and 45 females, among which 30 cases were aged and suffered from long term of illness, soreness and cold of waist and knees, lassitude, aversion to cold, impotence, spermatorrhea, loose stool, and frequent clear urination; 30 cases suffered from oral ulcer, aversion to cold and chilly limbs, physical lassitude, slightly white tongue fur, and deep pulse and inertia; 30 cases suffered from soreness of waist and leg weakness, physical aversion to cold, spasm in lower abdomen, difficult or frequent urination, pale and fat tongue, deep and thin pulse, phlegm and asthma, oedema, dermatophytosis, consumptive thirst, and chromatic diarrhea.

Usage and dosage: 8 g for each time, twice a day, dissolved in 200 ml of boiling water for administration.

Standards for Evaluating Efficacy:

Cure: clinical symptoms completely disappear, and normal life is resumed.

Effective: clinical symptoms partially disappear, and various physical signs are gradually improved.

Failed: no significant improvement on the symptoms is observed.

Statistics of results: 47 cases cured, effective for 33 cases, failed for 10 cases, that is, effective for 80 cases in total, with the overall effective rate of 88.89%.

Experiment Example 2: Sensory Evaluation

The solid drink prepared in Examples 1 to 5 was mixed with boiling water and then taken as test groups, and the mixed medicine liquid after the two times of decoction prepared and obtained in step (2) in the processing process of Example 5 as a control group. Samples of the test groups and the control group were set to have three repetitions. 20 professional sensory evaluators performed the sensory evaluation. The sensory evaluating and scoring standards are shown in Table 1, and the sensory evaluating results are shown in Table 2.

TABLE 1

Sensory Evaluating and Scoring Standards

| Item | Sensory Evaluation | Score |
|---|---|---|
| Color | dark | 1 |
| | suitable | 5 |
| | light | 1 |
| Odor | strong Chinese medicine smell | 1 |
| | slight Chinese medicine smell | 3 |
| | medicine fragrance | 5 |
| | relatively light | 3 |
| | light | 1 |
| Taste | bitter | 1 |
| | relatively bitter | 3 |
| | fragrant and sweet | 5 |
| | relatively sweet | 3 |
| | too sweet | 1 |
| Smoothness | smooth and lubricated | 5 |
| | sense of particles | 3 |
| | sense of scratching throat | 1 |
| | hard to swallow | 0 |
| Overall Evaluation | bad | — |
| | ordinary | — |
| | good | — |

It can be seen from the above test results that the mean scores of the color, odor, taste, and smoothness of the solid drink prepared in Examples 1 to 5 evaluated by the 20 professional sensory evaluators are higher than the scores of the control group. The results show that the solid drink provided in the present invention is greatly improved in the odor and taste over the medicine liquid obtained after decocting a Chinese medicine decoction piece, moreover, the sweet taste is added, and the taste and the smoothness are both substantially improved, quite suitable for daily drinking.

Experiment Example 3: Influence on Models of Yang-Deficiency Mice

Experiment method: 70 kunming mice, 35 males and 35 females, with a body weight of 200±15 kg, equally divided into 7 groups, namely, (1) normal control group; (2) yang-deficiency model group (hydrocortisone 25.0 mg/kg-+NS); (3) groups of Examples 1-5 (hydrocortisone 25.0 mg/kg-+ 0.3 g/kg of particles of the solid drink prepared in Examples 1-5). The groups of Examples 1-5 were subcutaneously injected with hydrocortisone while being fed with the particles of the solid drink by gavage. The hydrocortisone was injected subcutaneously for 8 d, and the gavage was continued for 10 d, and then the following indexes were observed on the 10th day: (1) autonomic activities: after 5 min of adaptation of each mouse, recording the times of activities of the mice in every 10 min; (2) low-temperature swimming time: putting the mice in water at a water temperature of 6-8° C., and observing the swimming time of the mice, where it indicated swimming disability when a mouse sunk down for 6 s but could not come out. The experiment results are shown in Table 3.

TABLE 3

Influence of Particles of Solid Drink of the Present Invention on Mouse Yang-deficiency Syndrome

| Group | Low-temperature Swimming Time (min) | Autonomic Activities (times/10 min) |
|---|---|---|
| Normal Control Group | 5.38 ± 1.11 | 728 ± 103 |
| Yang-deficiency Model Group | 3.96 ± 1.05 | 402 ± 128 |
| Example 1 | 5.23 ± 1.17 | 709 ± 142 |
| Example 2 | 5.46 ± 1.28 | 738 ± 151 |
| Example 3 | 5.19 ± 1.34 | 687 ± 154 |

TABLE 2

Sensory Evaluating Results

| Item | | Control Group | Example 1 | Example 2 | Example 3 | Example 4 | Example 5 | Mean |
|---|---|---|---|---|---|---|---|---|
| Sensory Evaluation/ score | Color | 36 | 95 | 96 | 90 | 92 | 96 | 93.8 |
| | Odor | 33 | 91 | 93 | 91 | 95 | 94 | 92.8 |
| | Taste | 52 | 89 | 97 | 93 | 94 | 91 | 92.8 |
| | Smoothness | 75 | 94 | 90 | 95 | 92 | 95 | 93.2 |
| | Mean | 49 | 92.25 | 94 | 92.25 | 93.25 | 94 | |
| Overall Evaluation/ number of person | Good | 8 | 19 | 19 | 20 | 18 | 20 | 19.2 |
| | Ordinary | 4 | 1 | 1 | 0 | 2 | 0 | 0.8 |
| | Bad | 8 | 0 | 0 | 0 | 0 | 0 | 0 |

TABLE 3-continued

Influence of Particles of Solid Drink of the Present Invention on Mouse Yang-deficiency Syndrome

| Group | Low-temperature Swimming Time (min) | Autonomic Activities (times/10 min) |
|---|---|---|
| Example 4 | 5.53 ± 1.35 | 698 ± 128 |
| Example 5 | 5.29 ± 1.33 | 735 ± 1.9 |

It can be seen from data in the above table that the low-temperature swimming time and the autonomic activities of the yang-deficiency mice are significantly increased in Examples 1-5 of the present invention, of which the effects are obviously superior to the yang-deficiency model group. The particles of the solid drink provided in the present invention have certain effects of regulating the yang-deficiency constitution.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A solid drink for regulating yang-deficiency constitution, comprising the following components of raw materials in parts by weight: *Perilla* 30-60, raspberry 35-55, *Lycium barbarum* 35-57, poria 30-54, cinnamon 35-55, fennel 20-40, ginger 33-55, dextrin 50-90, maltodextrin 23-45, soluble starch 20-44, and aspartame 0.15-0.35.

2. The solid drink for regulating yang-deficiency constitution of claim 1, comprising the following components of raw materials in parts by weight: *Perilla* 40-50, raspberry 41-49, *Lycium barbarum* 39-51, poria 38-47, cinnamon 41-52, fennel 25-35, ginger 37-50, dextrin 60-80, maltodextrin 27-40, soluble starch 25-39, and aspartame 0.2-0.3.

3. The solid drink for regulating yang-deficiency constitution of claim 1, comprising *Perilla* 45, raspberry 45, *Lycium barbarum* 45, poria 45, cinnamon 45, fennel 30, ginger 45, dextrin 69, maltodextrin 34, soluble starch 34, and aspartame 0.25.

4. The solid drink for regulating yang-deficiency constitution according to claim 1, wherein the solid drink is in a form of granular particles.

5. A method for processing a solid drink for regulating yang-deficiency constitution of claim 1, comprising the following steps:
  (1) preparing raw materials: mixing cinnamon, *Lycium barbarum*, ginger, *Perilla*, raspberry, poria, and fennel having undergone purification, cleansing, cutting, and grinding, for subsequent use;
  (2) decocting: decocting twice a mixture obtained in step (1) with addition of water, to obtain a Chinese medicine liquid;
  (3) concentrating: feeding the Chinese medicine liquid obtained in step (2) into a concentrator via a pipeline, to be concentrated into a thick paste;
  (4) wet granulating: mixing and stirring dextrin, maltodextrin, soluble starch, and aspartame to obtain a mixed excipient, and adding the thick paste obtained in step (3) to the mixed excipient, then stirring and granulating them.

6. The method for processing a solid drink for regulating yang-deficiency constitution of claim 5, wherein operations of the twice decocting processes in the step (2) are as follows:
  for the first time, adding water of 10 times the weight of the mixture obtained in the step (1), heating them for decocting and extracting the same, wherein timing is started when they are boiling, and after 1.5 hours of decoction and extraction, immediately feeding a medicine liquid through a pipeline filter by a pump into a stainless steel medicine liquid tank;
  for the second time, adding water of 8 times the weight of the mixture obtained in the step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

7. The method for processing a solid drink for regulating yang-deficiency constitution of claim 5, wherein a concentration temperature in the step (3) is 70-80° C., and a relative density of the resulted thick paste is 1.2-1.5 under a temperature condition of 50° C.

8. The method for processing a solid drink for regulating yang-deficiency constitution of claim 5, wherein the wet granulating in the step (4) comprises the following steps:
  (4.1) dry blending: putting dextrin, maltodextrin, soluble starch, and aspartame into an efficient mixing granulator to be mixed and stirred for 15 minutes, to obtain the mixed excipient;
  (4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time to form sized particles;
  (4.3) drying: putting the sized particles obtained in step (4.2) into a boiling dryer to be dried;
  (4.4) sizing for the second time: performing the second time of sizing by an oscillating machine.

9. The method for processing a solid drink for regulating yang-deficiency constitution of claim 8, wherein a 12-mesh screen is used in the first time of sizing, and a 10-mesh screen is used in the second time of sizing.

10. The method for processing a solid drink for regulating yang-deficiency constitution of claim 8, wherein in the drying process of step (4.3), a temperature of materials is kept at 70-80° C., and a moisture of final materials is kept below 5%.

11. The method for processing a solid drink for regulating yang-deficiency constitution of claim 8, wherein a step of selecting particles is further comprised after the second time of sizing, to select particles with 10-60 meshes.

* * * * *